(12) United States Patent
Koops

(10) Patent No.: US 7,811,246 B2
(45) Date of Patent: Oct. 12, 2010

(54) DEVICE FOR AUTOMATIC REGULATION OF THE CONCENTRATION OF GLUCOSE IN THE BLOOD OF A DIABETES PATIENT

(75) Inventor: Robin Koops, Goor (NL)

(73) Assignee: Inreda Diabetic B.V., Goor (NL)

( * ) Notice: Subject to any disclaimer, the term of this patent is extended or adjusted under 35 U.S.C. 154(b) by 0 days.

(21) Appl. No.: 12/091,841

(22) PCT Filed: Oct. 26, 2006

(86) PCT No.: PCT/NL2006/000574

§ 371 (c)(1),
(2), (4) Date: Sep. 15, 2008

(87) PCT Pub. No.: WO2007/049961

PCT Pub. Date: May 3, 2007

(65) Prior Publication Data

US 2009/0099507 A1    Apr. 16, 2009

(30) Foreign Application Priority Data

Oct. 26, 2005   (NL) .................................. 1030272

(51) Int. Cl.
*A61M 31/00*   (2006.01)
(52) U.S. Cl. ...................................................... 604/65
(58) Field of Classification Search ............. 604/65–67
See application file for complete search history.

(56) References Cited

U.S. PATENT DOCUMENTS

| | | | |
|---|---|---|---|
| 5,237,993 A | 8/1993 | Skrabal | |
| 5,474,552 A | 12/1995 | Palti | |
| 6,544,212 B2 * | 4/2003 | Galley et al. | 604/31 |
| 7,029,444 B2 * | 4/2006 | Shin et al. | 600/365 |
| 7,497,827 B2 * | 3/2009 | Brister et al. | 600/309 |
| 2003/0208113 A1* | 11/2003 | Mault et al. | 600/316 |
| 2003/0220579 A1* | 11/2003 | Mault | 600/531 |

FOREIGN PATENT DOCUMENTS

| | | |
|---|---|---|
| DE | 4123441 A1 | 1/1992 |
| WO | 9625088 A1 | 8/1996 |

* cited by examiner

*Primary Examiner*—Nicholas D Lucchesi
*Assistant Examiner*—Diva Ranade
(74) *Attorney, Agent, or Firm*—The Webb Law Firm

(57) ABSTRACT

A device for regulating the concentration of glucose in the blood of a diabetes patient includes a measuring component for measuring the concentration, a pump component for selectively introducing glucagon, or glucose instead, or insulin into the body of the patient, for instance by way of at least one hypodermic needle to be inserted into the body of the patient; and a control component which receives signals from the measuring component which are representative of the concentration and which control the pump component on the basis of at least one reference value for the concentration pre-entered into the control component and a program; wherein the device is embodied such that the measuring component and the pump component can be in substantially permanent contact with the bodily fluid or the blood of a patient.

6 Claims, 7 Drawing Sheets

| GLUCAGON | | | | |
|---|---|---|---|---|
| Glucagon settings | | | | |
| Pre-alarm eat | 4.50 | mmol/l | | |
| Pre-injection | 2.20 | mmol/l | 0.20 | ml |
| Pre-injection 2 | 1.80 | mmol/l | 0.35 | ml |
| Time delay glucagon injection | 5 | sec | | |
| Hysteresis switch off pump | 0.50 | mmol/l | | |
| Pre-alarm glucagon supply | 0.50 | ml | | |
| Alarm glucagon supply | 0.60 | ml | | |
| Shelf-life glucagon | 10 | days | | |

Injection request

○ ☐ Glocagon pump  0.20 ml in 00:10 min
　　 1 Glocagon unit  10 µl
　 ☐ Cancel Glocagon injection

[Enter] Ok　　[Esc] Back

Fig. 2

```
INSULIN
Insulin settings

Limit value insulin pre-injection      8.00  mmol/l  0.03  ml
Limit value insulin pre-injection 2   10.00  mmol/l  0.05  ml
Time delay insulin injection             5   sec
Hysteresis swich off insulin pump     0.50  mmol/l Pre-alarm insulin supply              0.50  ml
Alarm insulin supply                  0.50  ml
Shelf-life insulin                      30   days Injection request ○     ☐ Insulin pump quantity     0.20  ml in  00:10  min
            1 Insulin unit             2.5  µl
          ☐ Cancel insulin injection

[Enter] Ok        [Esc]  Back
```

Fig. 3

| ROBO | |
|---|---|
| Settings of the Robopump | |
| Last calibration on | mon 18jul2005 16:24 |
| Glucose present current | 27.0 nA |
| Glucose present measurement value | 4.29 mmol/l |
| Glucose calibration measurement | ☐ 4.92 mmol/l |
| Calibration coefficient | 0.16 |
| Pre-alarm calibration | 999.0 hours |
| Max. variation relative to average measerument | 0.00 mmol/l |
| Pre-alarm replacement needles & sensor | 550.0 hours |
| Average value of glucose measurement over | 00:10 min |
| Wait time following injection | 01:00 min |

Insulin injectioncurve

|  | Measured value | Injection quantity |
|---|---|---|
| Glucose target value | 6.500 mmol/l | 0.000 ml |
| Glucose point 1 | 10.000 mmol/l | 0.010 ml |
| Glucose point 2 | 20.000 mmol/l | 0.050 ml |
| Glucose point 3 | 30.000 mmol/l | 0.200 ml |

Calculate curve ☐   -0.0388   0.0093   -0.0006   0.0000

Glucagon injectioncurve

|  | Measured value | Injection quantity |
|---|---|---|
| Glucose point 4 | 4.000 mmol/l | 0.010 ml |
| Glucose point 5 | 2.500 mmol/l | 0.090 ml |
| Glucose point 6 | 0.100 mmol/l | 0.600 ml |

Calculate curve ☐   0.6359   -0.3660   0.0702   -0.0044

| Enter | Ok | | Esc | Back |

Fig. 5

| Safety | | |
| --- | --- | --- |
| Safety settings | | |
| Maximum insuline injection | 250.0 | µl |
| Maximum insuline injection 1 hour | 300.0 | µl/h |
| Maximum insuline injection 24 hours | 800.0 | µl/24h |
| Maximum glucagon injection | 500.0 | µl |
| Maximum glucagon injection 1 hour | 1000.0 | µl/h |
| Maximum glucagon injection 24 hours | 1500.0 | µl/24h |
| Reset emergency stop | ☐ | |
| Spoken alarm, number of repetitions | 5 | |
| Spoken alarm intervaltime | 10 | sec |

| Enter | Ok | | Esc | Back |

Fig. 7

DEVICE FOR AUTOMATIC REGULATION OF THE CONCENTRATION OF GLUCOSE IN THE BLOOD OF A DIABETES PATIENT

BACKGROUND OF THE INVENTION

Field of the Invention

The concentration of glucose in the blood of a diabetes patient is subject to strong fluctuations. In a healthy person regulation thereof takes place on the basis of the production of insulin in the pancreas. In patients with diabetes this healthy functionality is disrupted. In the case of an excessively high glucose concentration, for instance because the patient eats or drinks a large amount of carbohydrates in a relatively short time, this concentration must be reduced by administering a measured quantity of insulin by means of an injection or in other manner. In the case where the glucose concentration becomes too low, for instance because the patient has eaten or drunk no or few carbohydrates for some time, this concentration must be increased. This can take place by eating food with carbohydrates, such as a sandwich or a sugar cube.

Diabetes patients usually carry said ingredients with them. A diabetic may for instance carry a hypodermic syringe with insulin and a number of sugar cubes.

SUMMARY OF THE INVENTION

It is an object of the invention to improve the quality of life of a diabetic substantially by providing a device which carries out the desired regulation in fully automatic manner.

This object is realized according to the invention with a device of the stated type, which is characterized by measuring means for measuring the concentration of glucose in the blood of the diabetes patient;

pump means for selectively either introducing glucagon into the body of the patient or, if desired, introducing glucose into the bloodstream of the patient, or introducing insulin into the body of the patient, for instance by means of at least one hypodermic needle to be inserted into the body of the patient; and control means which receive signals from the measuring means which are representative of said concentration and which control the pump means on the basis of at least one reference value for said concentration pre-entered into the control means and a program such that said concentration is regulated;

wherein the device is embodied such that the measuring means and the pump means can be in substantially permanent contact with the bodily fluid or the blood of a patient.

The device can be embodied such that it can be applied for both diabetes type 1 and diabetes type 2 patients.

A short description of diabetes and the various forms thereof follows here by way of elucidation.

Diabetes is a syndrome characterized by a chronic increased concentration of glucose in the blood, and is associated with changes in the intermediary metabolism.

There are various causes of diabetes. The best known and most common forms are diabetes type 1 and diabetes type 2.

Type 1 diabetes often manifests itself during childhood and was therefore also called juvenile-onset diabetes. This form of diabetes is caused by an auto-immune process, which specifically destroys the beta cells and the islets of Langerhans in the pancreas. These islets of Langerhans are those areas in which the insulin is produced. This destruction results in a serious insulin deficiency necessitating a subcutaneous insulin therapy. Insulin is herein injected subcutaneously by means of a hypodermic needle.

The pathogenesis, the development of the disease, of type 2 diabetes, the most common form of diabetes, is complex and only partly clarified. In type 2 diabetes the capacity of the pancreas to produce insulin is reduced. In addition, there is almost always a reduced susceptibility to the effect of insulin on the target organs. This is also referred to as insulin resistance. This insulin resistance is closely related to obesity. Once a chronic hyperglycemia or diabetes has developed, many secondary changes occur which, although they do not form the cause of the disease per se, do cause a further increase in both insulin resistance and beta cell dysfunction. These secondary disorders are referred to as "glucose toxicity". The device can preferably be embodied such that the probe with the measuring means is embodied integrally with the hypodermic needle.

Once every 2 to 4 days the patient must replace the unit in question or the needle and the measuring means, in particular a glucose sensor, and replenish or replace the liquid cartridges in accordance usage.

BRIEF DESCRIPTION OF THE DRAWINGS

FIG. 2 depicts a glucagon settings screen of the software for the device according to an embodiment of the present invention;

FIG. 3 depicts an insulin settings screen of the software for the device according to an embodiment of the present invention;

FIG. 5 depicts a robopump settings screen of the software for the device according to an embodiment of the present invention;

FIG. 7 depicts a safety settings screen of the software for the device according to an embodiment of the present invention.

DETAILED DESCRIPTION OF THE INVENTION

The invention makes use of a glucose meter or sensor which measures either through the skin, subcutaneously, or directly in the blood of the patient. Use is further made of an insulin pump which is per se known but which is modified for application for the device according to the invention, and which is adapted for subcutaneous injection, or a pump which evaporates insulin via the skin such that it enters the bloodstream.

Since the above-skin techniques, although available, are at the moment not yet considered reliable enough for application, experimental and confidential use is made of subcutaneous techniques within the scope of the invention at the time of filing of this patent application.

The control unit and the software added thereto can be applied for all commercially available products suitable for this type of purpose (such as pumps, meters and so forth) which are relevant for the system.

Figure 4:
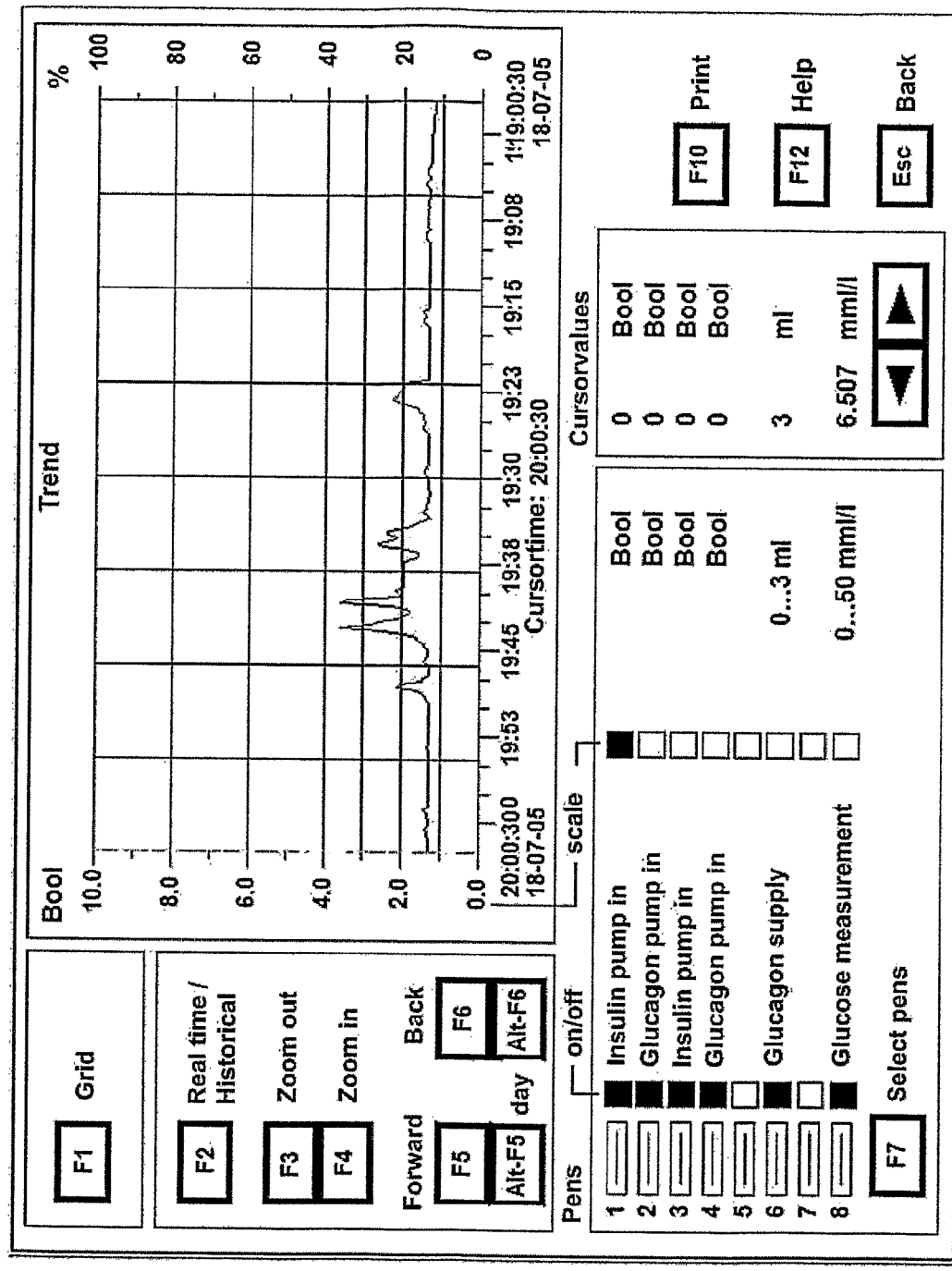
FIG. 4 depicts a recording screen of the software for the device according to an embodiment of the present invention.

The most important assumption is that the device according to the invention makes use of the current blood glucose values of the patient. In the device blood glucose values can be programmed which on the one hand indicate the lower limit, for instance 4.5 mmol/l (see FIG. 2), and on the other the upper limit, for instance 8.0 mmol/l (see FIG. 3). These programmed values are continuously compared to the current, i.e. measured values which the glucose meter transmits per time interval for programming, as can be seen in FIG. 4.

Figure 1:
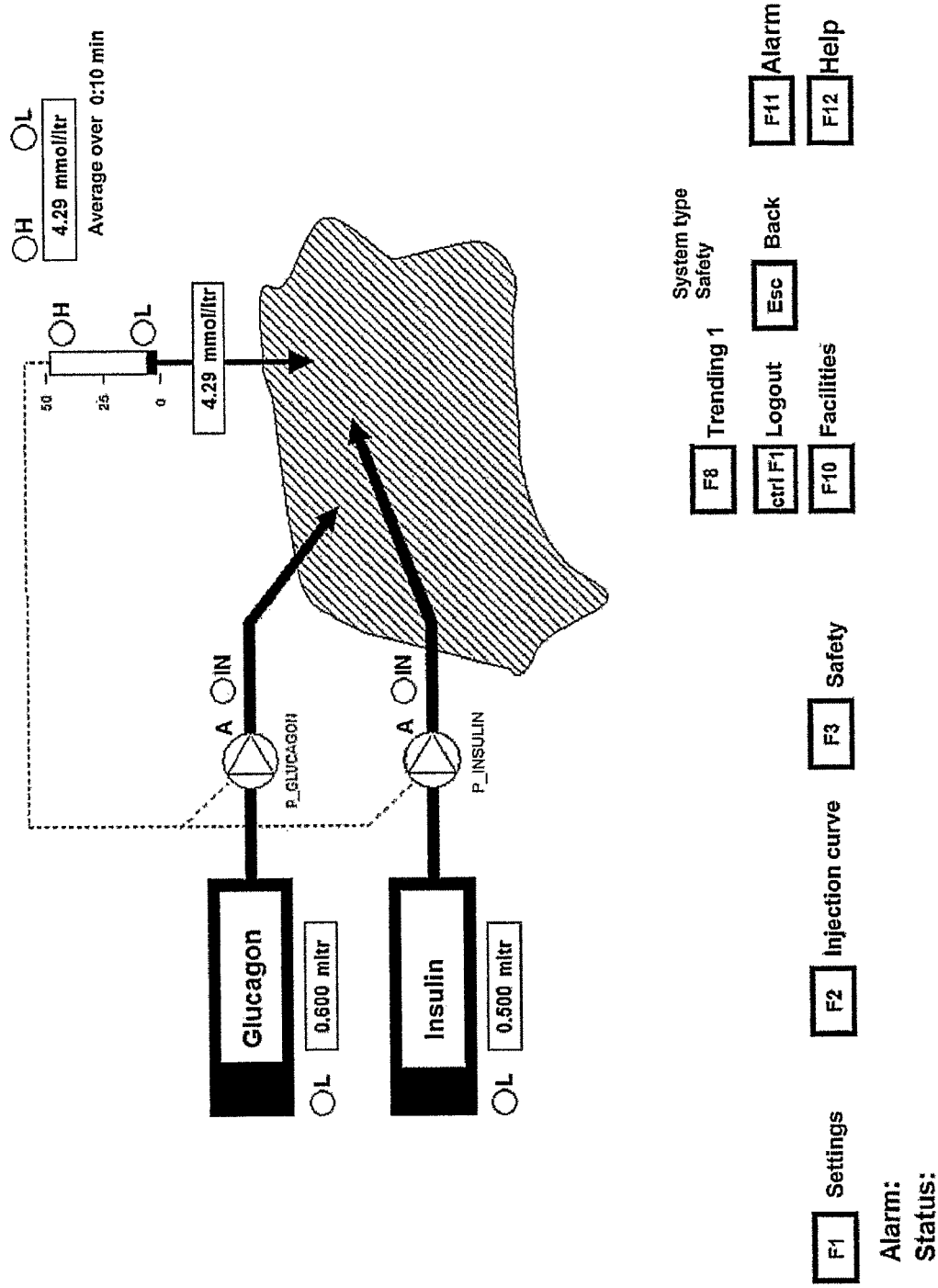
FIG. 1 depicts an opening screen of the software for the device for automatic regulation of the concentration of glucose in the blood of a diabetes patient according to an embodiment of the present invention.

The pump means comprise two pumps. These are controlled by the control means. The one pump contains a supply of insulin and the other pump contains a supply of glucagon, this as can be seen in the opening screen of the software (see FIG. 1).

Figure 6:
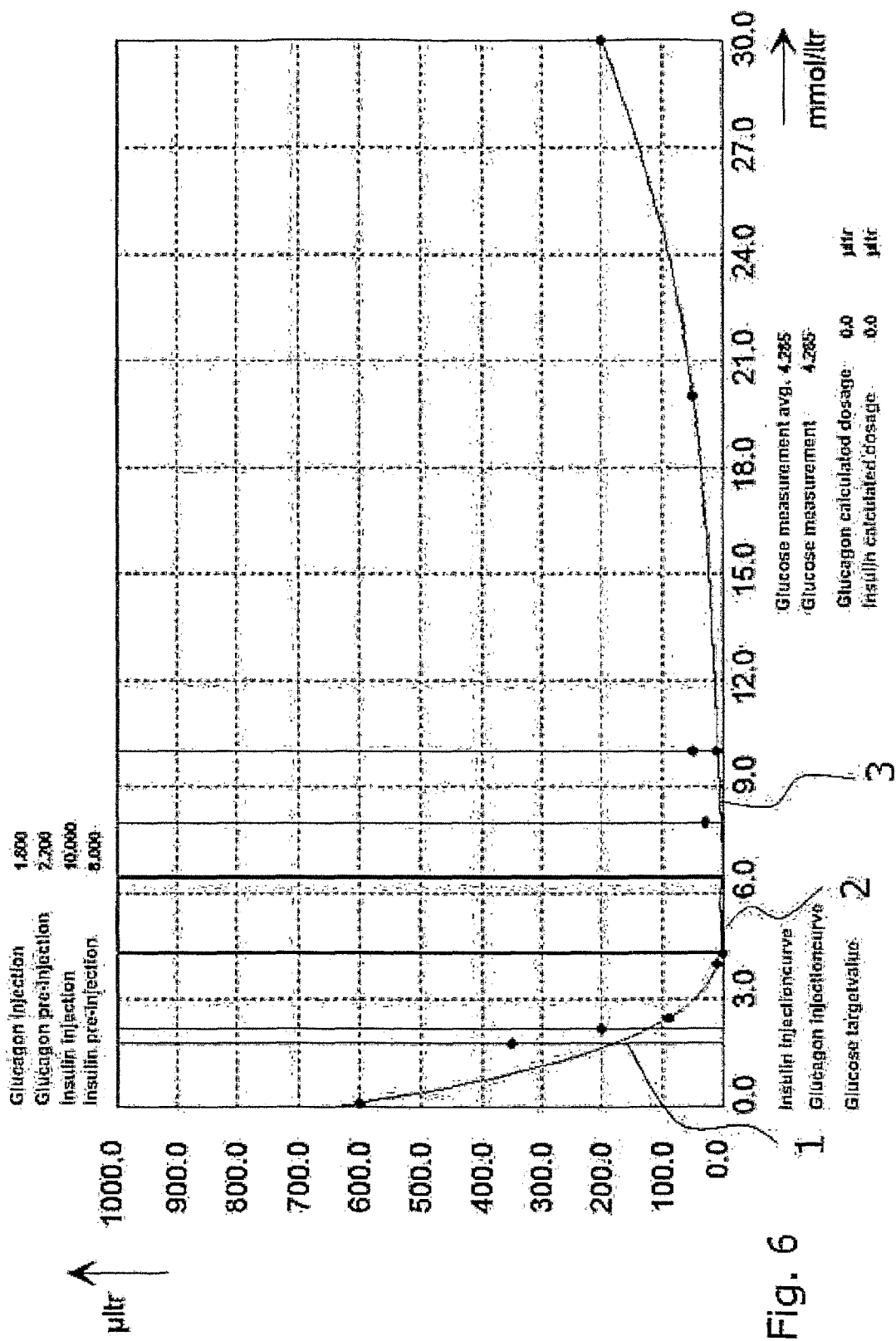
FIG. 6 depicts a programming curve of the software for the device according to an embodiment of the present invention.

The device according to the invention has three operating ranges, i.e.:

(1) At glucose values below the programmed lower limit a sound signal is in the first instance generated. The patient is hereby warned that the lower limit is being approached or has been exceeded. He/she can still anticipate this in good time by eating. In the case of a further fall glucagon is then injected in accordance with the set values (see FIGS. 2 and 5) and a curve to be programmed, ml(E)/fall mmol/l/time unit (see FIG. 6). A return within the normal zone is also made known, this with a "safe" signal.

(2) At glucose values between the lower limit and the upper limit the system is at "rest". Blood glucose values are however continuously watched and monitored and tendencies are recorded permanently (see FIG. 4). In the case of a strong fall or rise in the blood glucose values (fall or rise mmol/l/unit of time) this is anticipated in accordance with the inputted and the calculated data.

(3) At blood glucose values above the programmed upper limit insulin is introduced, in particular injected, as according to the set values (see FIGS. 3 and 5) and a curve to be programmed, ml(E)/rise mmol/l/unit of time (see FIG. 6), and a (different) sound signal is generated, whereby the patient is alerted that the upper limit is being approached or has been exceeded. If the fall in the blood glucose values starts at a determined speed (preferably adjustable) the supply of insulin is stopped. A return within the normal zone is also made known with the "safe" signal.

In this respect the device according to the invention can advantageously have the special feature that the control means comprise a program which incorporates, inter alia, an adjustable curve corresponding to the amount of insulin or glucagon respectively introduced into the body of the patient, and the nominal concentration of the glucose in the blood of the patient as a reaction thereto.

It is a particular advantage if the device has the feature that the control means store in a memory information relating to the introduced quantity of insulin or glucagon respectively, and in each successive case compare this information to the concentration of the glucose in the blood of the patient as a reaction thereto, also store this latter information in a memory, and use this latter information for metering the insulin or glucagon respectively, such that the control means are of the learning type.

Use is made within the application of the following parameters:

| | |
|---|---|
| Current blood glucose values | (measurement) |
| Unit of time (interval) | (programmable) |
| Number of measurements/unit of time | (programmable) |
| Lower limit | (programmable) |
| Upper limit | (programmable) |
| Pre-injection glucagon | (programmable) |

-continued

| | |
|---|---|
| Glucagon injection curve* according to formula 1 | (programmable, though person-dependent) |
| Pre-injection insulin | (programmable) |
| Insulin injection curve* according to formula 2 | (programmable, though person-dependent) |
| Rate of fall* according to formula 3 | (programmable, though person-dependent) |
| Formulae: | |
| 1) ml(E)/fall mmol/l/unit of time | (third-degree polynomial, to be programmed by means of three calibration points + the zero point = target value) |
| 2) ml(E)/rise mmol/l/unit of time | (third-degree polynomial, to be programmed by means of three calibration points + the zero point = target value) |

(*The sensitivity to insulin and glucagon of each patient can hereby be set precisely, irrespective of effort or rest; the current blood glucose values are then representative for the action of the system).

Elucidation of the Curve and Formulae

In ranges 1 and 3 injection takes place directly in accordance with the programmed polynomial (formula 1 and 2). In the case of stabilization, or if the measured value approaches the target value at a determined speed (adjustable), injection stops.

In ranges 1 and 3 pre-injection already takes place when the programmed lower and upper limit value (mm/l) is exceeded. The quantities of insulin or glucagon injected are derived from the relevant programmed polynomials, formula 1 (glucagon) or formula 2 (insulin), or from the set pre-injection values (FIGS. 2 and 3).

Safety

FIG. 7 shows the input screen for monitoring and safety. The safety system operates independently of the main operating system and neutralizes the injection part of the device according to the invention when the programmed limit values are exceeded. These limit values can be set subject to the individual person.

The measurement and trending of blood glucose values and associated alarm functions always remain active.

The software and hardware controls take a dual form so as to ensure the measurement, trending and alarm functions at all times.

Additional Development

In order to make the change of the needles and sensor every three days easier for the patient, these components can preferably be combined into one probe. The technical feasibility of this additional development has still to be tested, and a provisional design is shown in FIG. 8.

Fields of Application of the Device According to the Invention

Diabetes 1 and diabetes 2 patients

Intensive care patients with disturbed blood glucose values

Pregnant women with gestational diabetes

Diabetes patients in the broadest sense of the word

Any other medical application where medication or other substances must be injected in combination with, or subject to, measurements in blood or other bodily fluid, with the object of holding and monitoring a determined blood value within set limits.

LIST OF PARTS FIG. 8

1 Integrated unit
2 Connection insulin pump
3 Nozzle insulin pump
4 Connection glucose sensor
5 Glucose sensor
6 Connection glucagon pump
7 Nozzle glucagon pump
8 Integrated hypodermic needle According to a determined aspect of the invention, the device can have the special feature that the pump means comprise two pumps, one for glucagon or glucose and one for insulin, and that an individual hypodermic needle is added to each pump.

A great convenience of use is obtained with a device which has the special feature that the pump means comprise two pumps, one for glucagon or glucose and one for insulin, and that one shared hypodermic needle with two passages is added to the two pumps, wherein one serves for transport of glucagon or glucose and one for transport of insulin.

In respect of the hypodermic needles to be used, reference is made for the sake of completeness to the usual technical concept wherein use is made of a thin plastic tube which is inserted into the body of the patient by means of a sharp needle present therein, whereafter the needle is withdrawn and the tube remains behind and is then connected to the device. In the context of the present specification, said thin tube is also understood to mean "hypodermic needle".

The device according to the invention preferably has the special feature that the glucose sensor is carried by the or a hypodermic needle. Particularly in the embodiment in which use is made of only one hypodermic needle, the feeds for glucagon (or glucose) and for insulin, and also the glucose sensor, can hereby be introduced into the body of the patient in one operation.

The invention claimed is:

1. A device for regulating the concentration of glucose in the blood of a diabetes patient, the device comprising:
   a measuring component adapted for measuring the concentration of glucose in the blood of the diabetes patient;
   a pump component adapted for selectively introducing glucagon into a body of the patient or introducing glucose into the bloodstream of the patient, or introducing insulin into the body of the patient via at least one hypodermic needle to be inserted into the body of the patient; and
   a control component which receives signals from the measuring component which are representative of said concentration, and which controls the pump component on the basis of at least one reference value for said concentration pre-entered into the control component and a program such that said concentration is regulated, wherein the program incorporates an adjustable glucagon injection curve represented by a formula 1 (ml(E)/fall mmol/l/unit of time) and an adjustable insulin injection curve represented by formula 2 (ml(E)/rise mmol/l/unit of time) corresponding to an amount of glucagon or insulin, respectively introduced into the body of the patient, and the nominal concentration of the glucose in the blood of the patient as a reaction thereto,
   wherein the device is embodied such that the measuring component and the pump component can be in substantially permanent contact with a bodily fluid or the blood of a patient.

2. The device as claimed in claim 1, wherein the control component stores in a memory, information relating to the introduced quantity of insulin or glucagon respectively, and in each successive case compares this information to the concentration of the glucose in the blood of the patient as a reaction thereto, also store this latter information in a memory, and use this latter information for metering the insulin or glucagon respectively, such that the control component is of a learning type.

3. The device as claimed in claim 1, wherein the pump component comprises two pumps, one for glucagon or glucose and one for insulin, and an individual hypodermic needle is added to each pump.

4. The device as claimed in claim 1, wherein the pump component comprises two pumps, one for glucagon or glucose and one for insulin, and one shared hypodermic needle with two passages is added to the two pumps, wherein one passage serves for transport of glucagon or glucose and one for transport of insulin.

5. The device as claimed in claim 1, wherein the measuring component comprises a glucose sensor to be placed in the body of the patient.

6. The device as claimed in claim 5, wherein the glucose sensor is carried by a hypodermic needle.

* * * * *